United States Patent [19]
Quinn

[11] Patent Number: 5,865,816
[45] Date of Patent: Feb. 2, 1999

[54] PERCUTANEOUS ENDOSCOPIC GASTROSTOMY TUBE ASSEMBLY AND METHOD

[75] Inventor: David G. Quinn, Grayslake, Ill.

[73] Assignee: C. R. Bard, Inc., Murray Hill, N.J.

[21] Appl. No.: 850,636

[22] Filed: May 2, 1997

Related U.S. Application Data

[60] Division of Ser. No. 734,630, Oct. 18, 1996, which is a continuation-in-part of Ser. No. 583,930, Jan. 11, 1996, abandoned.

[51] Int. Cl.⁶ .................................................. A61M 25/00
[52] U.S. Cl. ........................... 604/280; 604/264; 604/96
[58] Field of Search .............................. 604/96, 100, 103, 604/116, 117, 256, 264, 280, 282, 283, 905

[56] References Cited

U.S. PATENT DOCUMENTS

| | | |
|---|---|---|
| 3,915,171 | 10/1975 | Shermeta . |
| 4,261,363 | 4/1981 | Russo . |
| 4,356,824 | 11/1982 | Vazquez . |
| 4,419,094 | 12/1983 | Patel . |
| 4,435,174 | 3/1984 | Redmond et al. . |
| 4,533,349 | 8/1985 | Bark . |
| 4,543,089 | 9/1985 | Moss . |
| 4,576,603 | 3/1986 | Moss . |
| 4,594,074 | 6/1986 | Andersen et al. . |
| 4,642,092 | 2/1987 | Moss . |
| 4,645,492 | 2/1987 | Weeks . |
| 4,666,433 | 5/1987 | Parks . |
| 4,685,901 | 8/1987 | Parks . |
| 4,699,616 | 10/1987 | Nowak et al. . |
| 4,701,163 | 10/1987 | Parks . |
| 4,717,385 | 1/1988 | Cameron et al. . |
| 4,795,430 | 1/1989 | Quinn et al. . |
| 4,798,592 | 1/1989 | Parks . |
| 4,834,712 | 5/1989 | Quinn et al. . |
| 4,900,306 | 2/1990 | Quinn et al. . |
| 4,932,943 | 6/1990 | Nowak . |
| 4,981,471 | 1/1991 | Quinn et al. . |
| 4,986,815 | 1/1991 | Schneider . |
| 5,073,166 | 12/1991 | Parks et al. . |
| 5,073,170 | 12/1991 | Schneider . |
| 5,125,897 | 6/1992 | Quinn et al. . |
| 5,267,967 | 12/1993 | Schneider . |
| 5,267,969 | 12/1993 | Hirsch et al. . |
| 5,308,325 | 5/1994 | Quinn et al. . |
| 5,318,530 | 6/1994 | Nelson, Jr. .............................. 604/270 |
| 5,324,260 | 6/1994 | O'Neill et al. .......................... 604/100 |
| 5,342,321 | 8/1994 | Potter . |
| 5,370,625 | 12/1994 | Shichman . |
| 5,439,444 | 8/1995 | Andersen et al. . |
| 5,451,212 | 9/1995 | Andersen . |
| 5,484,420 | 1/1996 | Russo . |
| 5,662,622 | 9/1997 | Gore et al. .............................. 604/282 |

FOREIGN PATENT DOCUMENTS 0 574 961 A1  12/1993  European Pat. Off. .

OTHER PUBLICATIONS

"AMT . . . The Leader In Innovative Gastrostomy Feeding System" (1 page), Undated.
"The AMT Button" (1 page), Undated.
"Care Giver Guide For The Corpak Button" (1 page), Undated.

(List continued on next page.)

*Primary Examiner*—John D. Yasko
*Attorney, Agent, or Firm*—Richard G. Lione; Brinks Hofer Gilson & Lione

[57] ABSTRACT

A corporeal access tube assembly includes a tube segment containing a coil spring. A retention balloon is secured to the tube segment around a portion of the segment. A deflation lumen extends through the tube segment from a predetermined location in said tube segment which is spaced from one end of the tube segment to a location adjacent the balloon where it is in fluid communication with the balloon. A set connector has a fitting with external threads which is threaded into the one end of the tube segment and into the coil spring.

11 Claims, 7 Drawing Sheets

OTHER PUBLICATIONS

"For the Past seven years, we've proved that keeping a low profile can help you come out on top." (1 page), Undated.

"MIC–KEY Feeding Kit" (2 pages), Undated.

"The Medical Innovator™ Presents: Pee Wee™ A Low Profile Gastrostomy Feeding Kit" (2 pages), Undated.

"Comparing Low–Profile Gastrostomy Tubes" (3 pages), Dec., 1993.

"Stellar Performance" (2 pages), Undated.

Corpak "Inflation/Deflation Machanics" (1 page), Dec. 1991.

"Incomparable Moss® Tubes . . . " (1 page), Undated.

"Moss Decompression—Feeding Catheters" (1 page), Undated.

Brochure entitled, "AMT Presents a Giant Step Forward in Innovation The One Step Button," 1 page, published by Applied Medical Technology, Inc., Undated.

Brochure entitled, "Innovation is Back, AMT Presents . . . P.R.G.® Gastrostomy Feeding Systems," 1 page, published by Applied Medical Technology, Undated.

Brochure entitled, "Stellar Performance," 2 pages, Undated.

Brochure entitled, "Polyurethane, Collapsibility, Locking Systems, Flexible Systems," 2 pages, Undated.

Brochure entitled, "Introducing EntriStar™ Single Pass P.E.G./J," 3 pages, published by Sherwood Medical, Undated.

Brochure entitled, "Bard® Silicone PEGs, Bard® Guidewire System & Ponsky™ Pull, PEG," 1 page, published by Bard, Undated.

Brochure entitled, "FLEXIFLO® New Inverta–PEG™ Gastrostomy Kit With Roll–Tip Bumper," 2 pages, published by Ross Products Division, Abbott Laboratories, Undated.

Brochure entitled, "MIC Gastrostomy Tube," 3 pages, Undated.

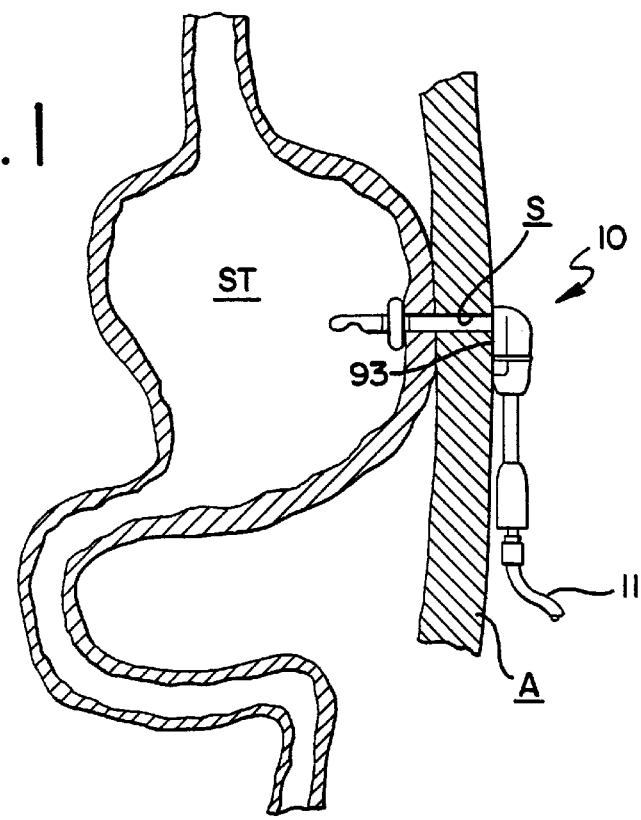
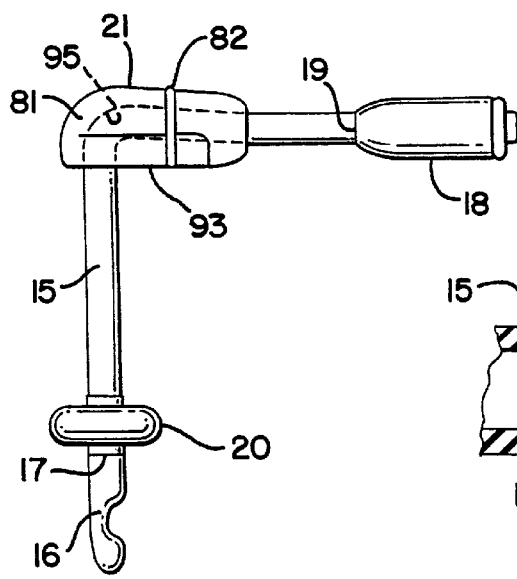
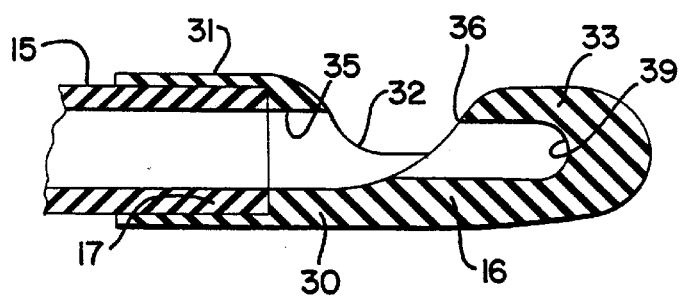
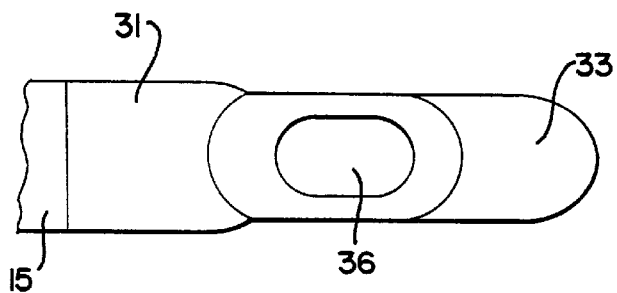

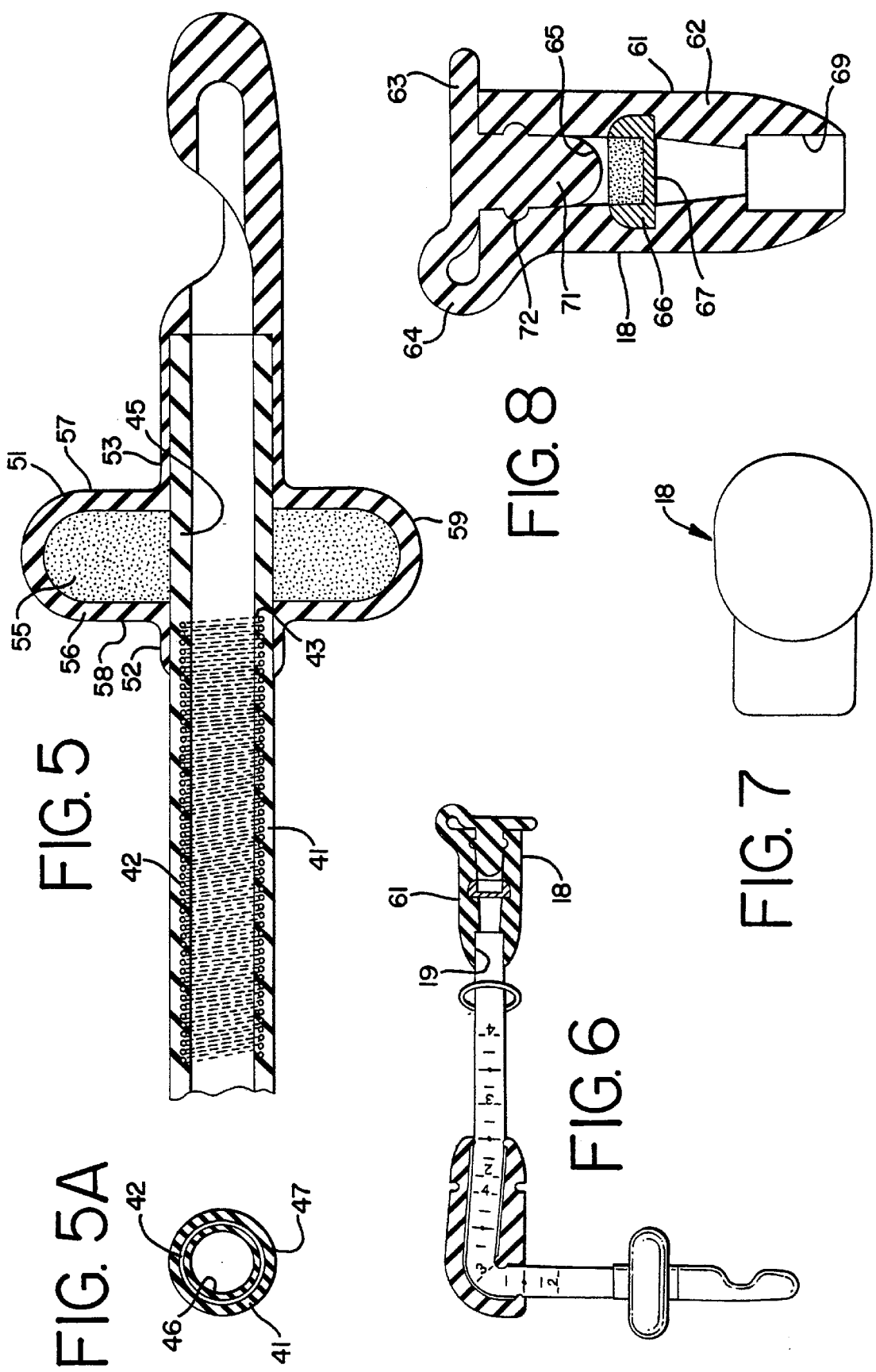

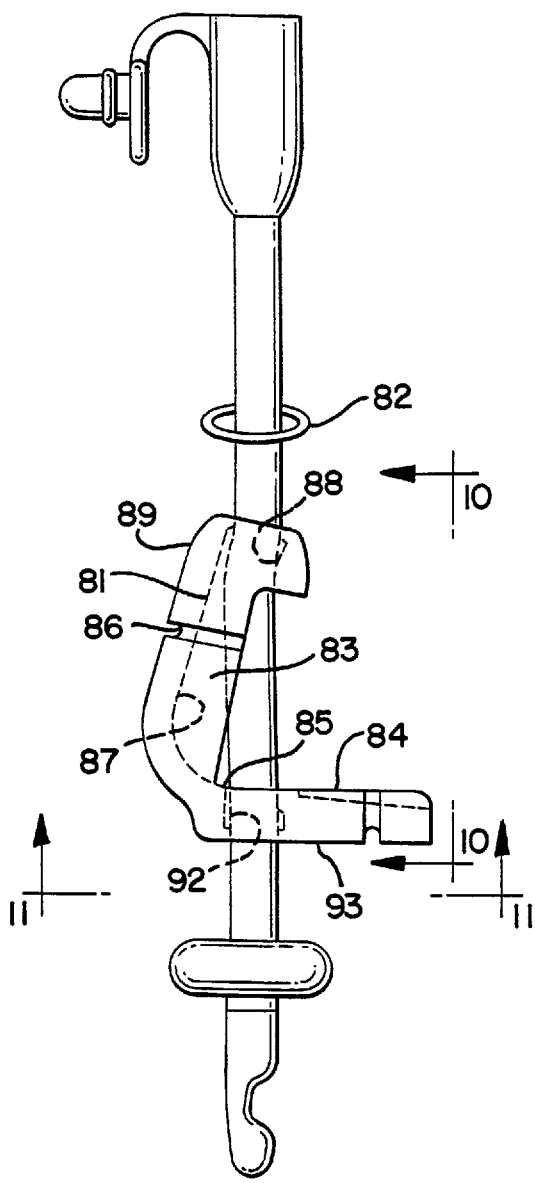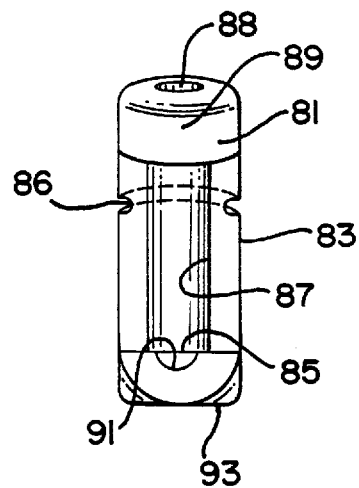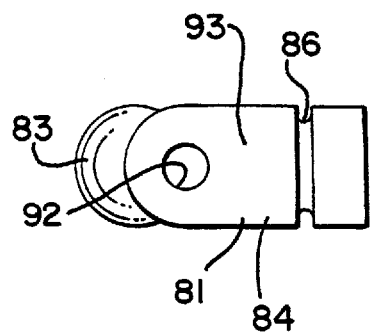

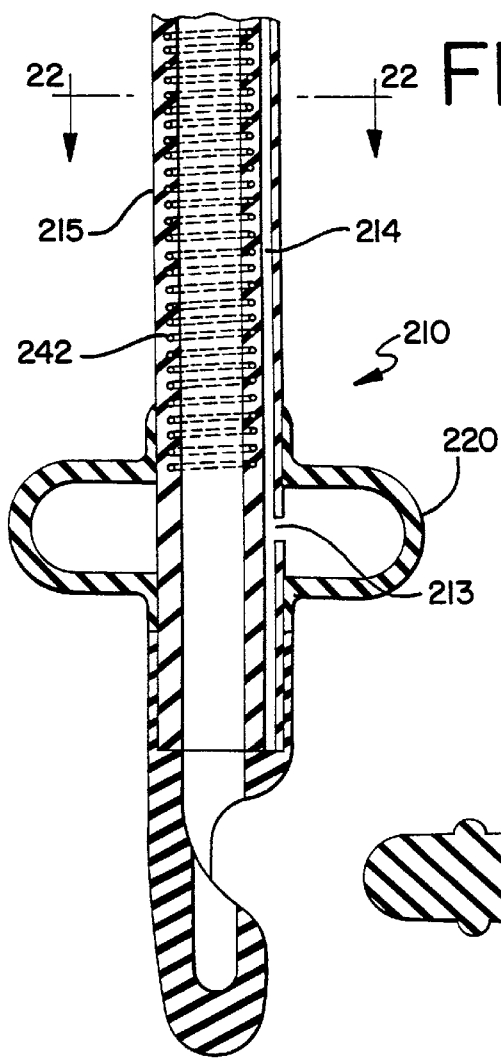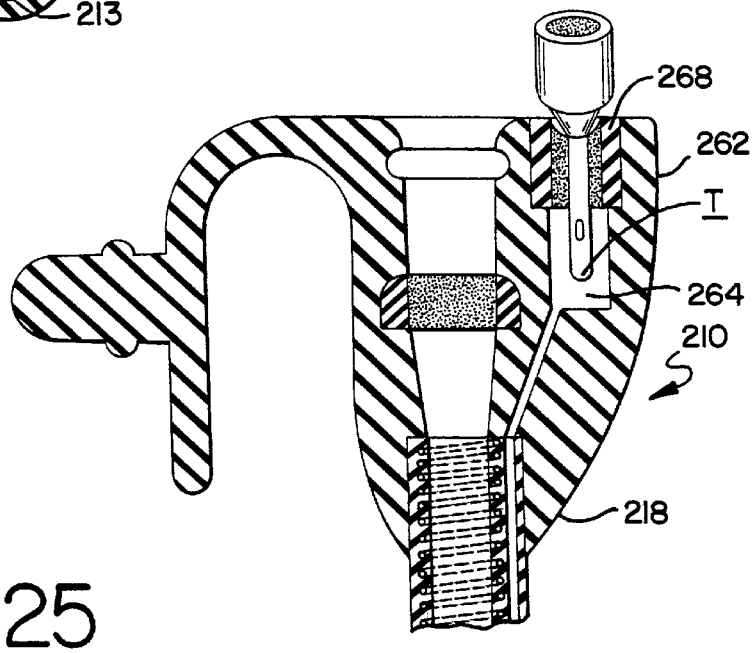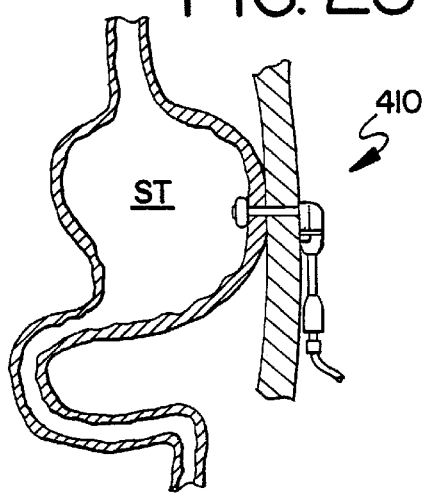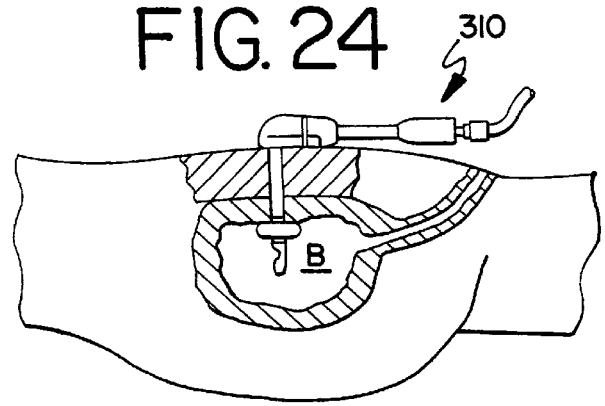

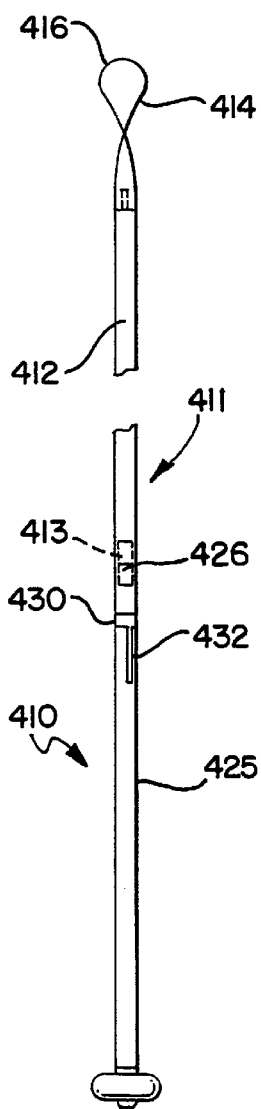
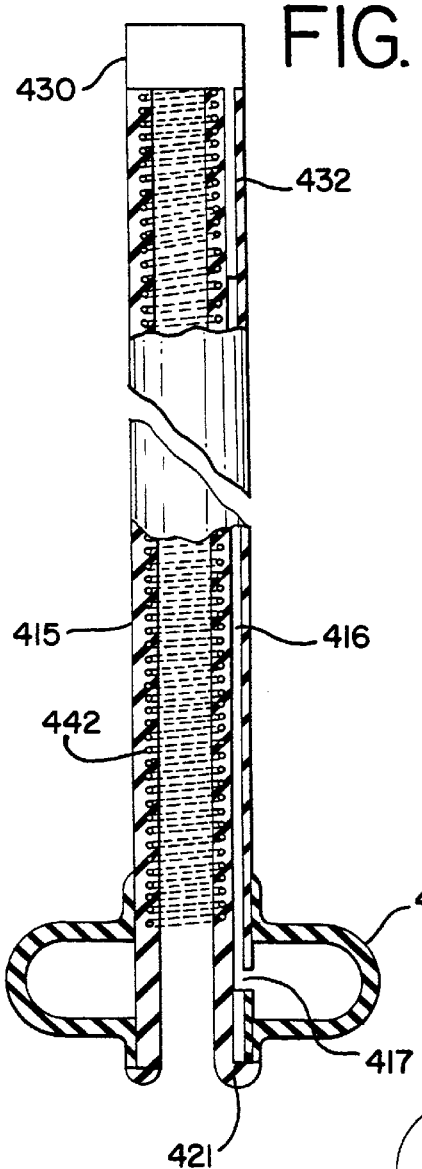
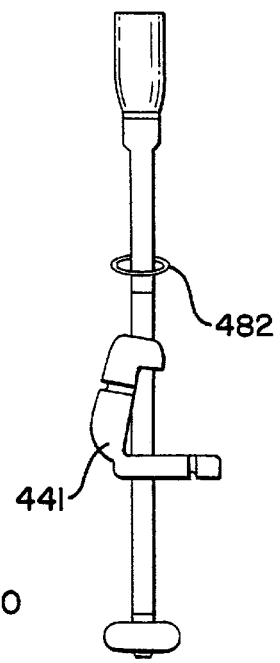
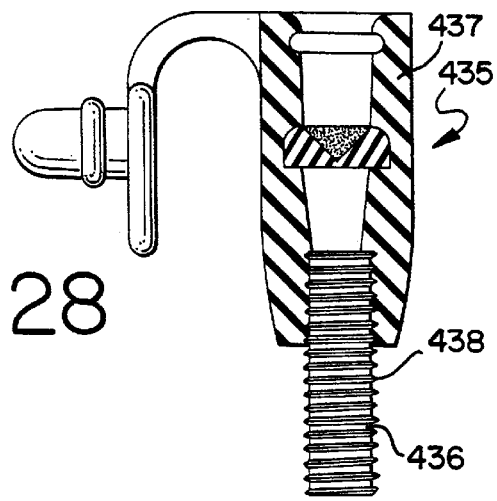

PERCUTANEOUS ENDOSCOPIC GASTROSTOMY TUBE ASSEMBLY AND METHOD

RELATED APPLICATIONS

This is a division of pending application Ser. No. 08/734,630, filed Oct. 18, 1996, and entitled Corporeal Access Tube Assembly and Method, which is a continuation-in-part of application Ser. No. 08/583,930, filed Jan. 11, 1996 and entitled Replacement Gastronomy Tube. The later application is now abandoned.

FIELD OF THE INVENTIONS

These inventions relate generally to medical catheters. They relate particularly to catheters used to access either the stomach and/or intestine, or the bladder, through a stoma or ostomy in the abdominal wall.

BACKGROUND OF THE INVENTIONS

The need to artificially introduce food into the gastrointestinal tracts of individuals who can not eat, or will not eat, has been well known throughout and even prior to this century. Before the mid-1970's, feeding was done nasogastrically with red rubber or polyvinylchloride feeding tubes. The use of enteral feeding by means of nasogastric tubes expanded dramatically in the late 1970's with the introduction of tubes constructed of either silicone rubber or polyurethane. Being constructed of stronger materials, these tubes incorporated thinner walls, and were therefore smaller in outside diameter. These smaller tubes were easier to insert and more comfortable for the patient, and their introduction resulted in a very rapid growth of enteral nutrition via the nasogastric route, and increased interest in enteral nutrition in general.

By the 1980's problems with nasogastric feeding were recognized by clinicians and the advantages of direct gastrostomy access into the stomach through the abdominal wall had been described by Vazquez in U.S. Pat. No. 4,356,824, and by Moss in U.S. Pat. No. 4,543,085. Refinements in securing gastrostomy tubes in the patient were described by Parks in U.S. Pat. No. 4,666,433 and in U.S. Pat. No. 4,685,901.

The 1980's also saw the refinement of methods for forming the gastrostomy stoma. Prior to the 1980's, the stoma or gastrostomy was formed surgically by the Stamm procedure, which required a surgical laporatoratomy to insert the tube, usually a latex urologic Foley retention catheter. A new method, called a "PEG", or Percutaneous Endoscopic Gastrostomy, eliminated the need for a surgical gastrostomy to place the gastrostomy tube and dramatically expanded the interest in the use of direct gastrostomy tubes. The advantages of PEGs and the PEG technique were described by Quinn et al in U.S. Pat. No. 4,795,430. The word "PEG" is used herein to identify both the tube and the procedure.

Gastrostomy tubes can generally be organized into three main groups, the third of which includes two subgroups:
1. SPECIALTY TUBES placed at the time of gastric surgery by the Stamm technique. The Moss and Vazquez patent tubes are examples of this type.
2. PEG tubes which are used to form the initial stoma or gastrostomy.
3. REPLACEMENT TUBES which are used to replace the PEG tube after a period of time because the PEG has worn out with use, or because a device which is more specific to the patient's need is required. These tubes are inserted into the original stoma created by either the PEG or the Stamm technique.
   a. LOW PROFILE REPLACEMENT TUBES which are preferred for active patients who wish to conceal the tube's outer fitments during periods when they are not receiving feeding formula. The background for this type of replacement tube is described by Quinn et al in U.S. Pat. No. 5,125,897.
   b. SIMPLE REPLACEMENT tubes which are less complicated and less expensive are used for patients who are not active and have no need to hide their device. These devices are direct modifications of the original urologic Foley catheters used in early gastrostomies. They are described by Parks in U.S. Pat. No. 4,666,433.

With some exceptions within individual designs, gastrostomy tubes or tube assemblies of the aforedescribed types each incorporate the following seven features or components:

1. A tube to carry the enteral feeding formula into the stomach and or the intestine.
2. An outflow port in the distal end of the tube. The port or ports may be incorporated in the end or the side wall of the tube. They may also be incorporated in a separate, molded bolus fastened to the distal end of the tube.
3. An administration set connector attached to the proximal end of the tube, which is outside of the patient.
4. A distal end retention device to hold the tube in the stomach, e.g., an inflatable balloon or a molded retention shape which can be deformed with a stylet for insertion and removal.
5. An external bolster to secure the tube at the point where it exits the skin. This bolster maintains the proper distance between the external bolster and the internal retention device, a distance corresponding to the combined thickness of the individual patient's skin, abdominal wall and stomach wall at the site of the gastrostomy.
6. An anti-reflux valve to prevent leakage of gastric acids from the patient when the administration set is being changed or when violent coughing causes excessive back pressure.
7. A measurement system to measure the patient's abdominal wall thickness so that the tube length between the retention device and the external bolster can be adjusted to match this thickness.

Just as gastrostomy tubes or tube assemblies are used for enteral feeding, so suprapubic catheter tubes or tube assemblies are used to administer drugs to, or drain urine from, the bladder. Such tubes or tube assemblies comprise the same seven features or components referred to above in the context of gastronomy tubes or tube assemblies. However, they access the bladder through a stoma formed in the abdominal wall above the bladder or pubic area.

SUMMARY OF THE INVENTION

The present inventions seek to resolve problems which clinical practice has shown to be inherent in the aforedescribed seven features or components of different types of known gastrostomy and suprapubic catheterization tubes or tube assemblies. As described in the background materials, there is now little key component design commonality between PEGs, low profile replacement tubes and simple replacement tubes, for example. The inventions disclosed herein embody improvements which can be incorporated into all of the tube types, thereby providing a common component system for all gastrostomy and superpubic catheterization tubes.

In doing so these inventions overcome the major problems associated with existing tubes, which are:

Difficulty of insertion and removal.

Difficulty of obtaining accurate measurement of required tube depth.

Lack of durability of internal retention devices.

Incompatibility of replacement gastrostomy tubes with PEGs.

Valve failure.

Infection of the stoma.

Difficulty in cleaning of the stoma.

The need for many tube sizes.

Inability to secure the tube adequately with an external bolster.

The need for special administration sets.

These problems manifest themselves in tube components as follows:

1. THE TUBE. Silicone and polyurethane are the materials of choice for these tubes. Silicone is softer and more compliant than polyurethane. Silicone has a lower modulus of elasticity than urethane. Softness is desirable in medical catheters. However, softness also increases the ability to kink and collapse, which are undesirable characteristics. These problems have heretofore been addressed by making tube walls thicker in silicone tubes or by constructing the tubes from the stronger, but less flexible, polyurethane. The designer has had to make a choice between a smaller, but less flexible, urethane tube and a larger, softer silicone tube.

Flexibility, resistance to kinking and resistance to collapsing are characteristics which are particularly important in gastrostomy and suprapubic catheterization tubes. Because these tubes exit the body perpendicular to the skin, it is desirable to be able to bend them as close to a right angle as possible so that they can lie next to the skin. This problem is addressed in Quinn et al U.S. Pat. No. 4,834,712. In addition, some forms of gastrostomy tubes have extensions which feed out of the stomach into the duodenum or jejunum. These tube extensions must be able to negotiate from one to five acute angle turns, depending whether they are placed in the duodenum or further into the jejunum. Tubes with a higher modulus, i.e., less flexible tubes, can dig into the side walls of the intestine and resist making the required tight turns as they move through the intestine.

2. OUT FLOW PORT IN DISTAL END OF TUBE. The problems with conventional nasogastric feeding tube outlet ports as to insertion, flow and clogging are described by Andersen et al. in U.S. Pat. No. 4,594,074. These problems are also common to gastrostomy tubes.

3. ADMINISTRATION SET CONNECTOR. Existing low profile tubes have administration set connectors which exit perpendicular to the patient's skin. This configuration is described in Quinn et al. U.S. Pat. No. 5,125,897. To prevent the administration set from kinking and twisting, special sets with right angle connectors must be used so that the administration set tubing can lie comfortably on the patient's abdomen.

4. DISTAL END RETENTION DEVICE TO HOLD THE TUBE IN THE STOMACH or bladder. Tubes with inflatable silicone retention balloons are easy to insert because the uninflated balloons are formed completely flat against the tube wall. However, they are unreliable because the silicone balloon walls which are stretched thin tend to break easily. In addition they must incorporate a second inflation lumen in the tube to access the balloon. This feature makes the tube larger and also requires the incorporation of a balloon inflation valve which adds cost and bulk to the product.

Pre-formed, molded internal retention devices must be deformed with a stylet and are difficult to insert and remove. They are generally reliable once they are in place, however.

5. EXTERNAL BOLSTER. Existing technology for bolsters is well known, as the aforementioned prior art illustrates. Some bolsters secure the tube, but do not bend it at a right angle to position it out of the way, next to the skin. Others secure and bend it at a right angle, but are rigid parts which can be uncomfortable for the patient. None of these rigid bolsters achieve full, right-angle bending of the tube due to the stiffness of the tubing.

6. ANTI-REFLUX VALVE. Existing valves include flapper valves which clog and malfunction. Furthermore, it is often necessary to open the valve to decompress the stomach or bladder, so location of the valve is also important. Some gastrostomy valves are positioned so that special decompression sets are required to activate them if feeding is not taking place.

7. TUBE MEASUREMENT AND SIZING. PEGs and simple gastrostomy tubes, for example, are sized to the patient after they are inserted. The position of the external bolster is approximated by simultaneously tugging on the internal retention member and then pushing the external member down on the skin. This is an imprecise method. Low profile replacement tubes have separate stoma depth measuring tools which are pre-inserted into the stoma. The clinician then selects a tube which corresponds to this measurement from a large selection of tube lengths. These tubes can not be adjusted for a change in patient size.

The present inventions include a reinforced silicone tube which has the same modulus as an unreinforced silicone tube and walls which can not be collapsed or kinked. The invention has walls which are approximately the same thickness as a comparable urethane tube. The new tube is therefore superior to both silicone and urethane.

The present inventions include a one piece anti-reflux slit valve located in the set which automatically opens flow in either direction when the luer of a regular set connector is inserted. It cannot be damaged by a stylet.

The present inventions include a pre-formed, pre-inflated silicone balloon with unique deformation characteristics for both insertion and removal. Because it is pre-formed, the balloon walls are approximately 0.012 to 0.030 inches thick during use, versus the 0.004 inch thick walls of inflated balloons. It also has unique retention qualities in relation to much larger retention devices.

The present inventions include a simple, silicone bolster which both secures the catheter and bends it at a right angle to the patient's skin. The bolster presents minimum bulk and maximum access to the stoma for air circulation and cleaning. It is secure but can be easily adjusted as the patient's condition changes.

The present inventions include a system which eliminates the need for pre-measurement devices and greatly reduces the number of necessary sizes for low profile replacement tubes. For the first time, it also provides a means for precisely measuring the bolster position. This pre-measurement and precise bolster positioning are accomplished by a unique tube marking system in combination with the bolster.

In addition to the aforedescribed, these improvements and others are also embodied in a PEG tube and insertion assembly invention. This invention incorporates most of the components of the low profile replacement tube. After insertion, the PEG tube assembly which remains embodies all of the features of the replacement tube.

The PEG tube assembly is inserted by the same method as a conventional PEG. Therefore no stylet is required. In addition, because the internal retention balloon is inserted in its inflated state, the feeding set connector has no inflation/deflation valve or lumen.

After insertion into the stomach, the tube is cut off at a predetermined point indicated by a wide black marker band encircling the PEG tube. An inflation/deflation lumen in the wire reinforced PEG tube is occluded by a plug extending approximately 5 centimeters below the black marker band. This plug retains the air in the retention balloon when the tube is subsequently cut at the marker band.

After the tube is cut at the marker band, the external bolster of the invention and retention ring are slipped over the tube. The feeding set connector is then threaded into the tube. Tube depth is adjusted and the external bolster is anchored. The device is now ready to function as a low profile gastrostomy tube, just like the replacement tube.

To remove the tube, it is cut off at a marker line below the marker band. This line is normally positioned 10 to 15 centimeters from the retention balloon. The marker line is below the air inflation/deflation line plug, so the air line is opened when the tube is cut. The open air line allows air to escape from the balloon during removal, thereby allowing the balloon to deform as it is being pulled out of the stoma.

BRIEF DESCRIPTION OF THE DRAWINGS

The foregoing and other objects of these inventions are illustrated more or less diagrammatically in the drawings, in which:

FIG. 1 is an illustration of a replacement tube assembly embodying features of the inventions, with the tube assembly in place accessing a patient's stomach;

FIG. 2 is an enlarged side elevational view of the replacement tube assembly illustrated in FIG. 1;

FIG. 3 is a longitudinal sectional view through the bolus end of the replacement tube assembly illustrated in FIGS. 1 and 2;

FIG. 4 is a top plain view of the bolus end illustrated in FIG. 3;

FIG. 5 is a longitudinal sectional view, similar to FIG. 3, showing more of the replacement tube assembly embodying features of the inventions;

FIG. 5A is sectional view taken through the tube assembly of FIG. 5, showing the coil spring.

FIG. 6 is a side view, similar to FIG. 2 but partially in section illustrating a near-completely assembled replacement tube assembly embodying features of the inventions;

FIG. 7 is an end view of the set-connector cap in the replacement tube assembly of FIGS. 1–6;

FIG. 8 is an enlarged, side view of a set-connector for the replacement tube assembly of FIGS. 1–6, partially in section;

FIG. 9 is a side elevational view of a replacement tube assembly embodying features of the inventions, illustrated in its unassembled form prior to insertion through a stoma formed in a patient's stomach;

FIG. 10 is a front elevational view of the bolster component for the replacement tube assembly of FIG. 9 taken along line 10—10 of FIG. 9, with the tube component removed;

FIG. 11 is a bottom plan view of the bolster component of FIG. 10, taken along line 11—11 of FIG. 9 with the tube component removed;

FIG. 21 is a longitudinal sectional view through the bolus end of a replacement tube assembly embodying features of another form of the inventions, a form in which the balloon is accessed by an inflation and deflation lumen;

FIG. 22 is a sectional view taken along line 22—22 of FIG. 21;

FIG. 23 is a sectional view through the set connector for the form of replacement tube assembly shown in FIG. 21;

FIG. 24 is a view similar to FIG. 1 illustrating the inventions embodied in a suprapubic catheter tube assembly;

FIG. 25 is a view similar to FIG. 1 illustrating the inventions embodied in a PEG tube assembly;

FIG. 26 is a side elevational view of a PEG and insertion tube assembly embodying features of the present inventions;

FIG. 27 is an enlarged side elevational view of a portion of the PEG tube assembly after it is severed from the assembly of FIG. 25;

FIG. 28 is a side elevational view of a feeding set adaptor ready for mating with the PEG tube assembly of FIG. 27; and FIG. 29 is a side elevational view of the assembled PEG tube after a feeding set adaptor has been mated.

DESCRIPTION OF THE PREFERRED EMBODIMENT

Figure 12:
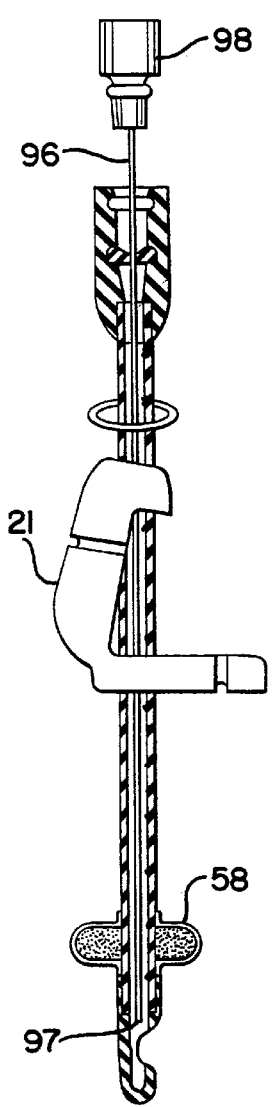
FIG. 12 is a longitudinal section taken through the replacement tube assembly of FIG. 9 showing a stylet partially inserted and the tube assembly about to be inserted through a stoma.

Referring now to the drawings, and particularly to FIG. 1, the inventions disclosed to are embodied here in a replacement gastrostomy tube assembly shown generally at 10. The tube assembly 10 is shown in place, extending through a stoma S in a patient, from a feeding formula supply tube 11 outside the patient's abdominal wall A to inside the patient's stomach ST. The stoma S may be formed in a conventional manner by one of several well-known procedures hereinbefore referred to.

The tube assembly 10 is a replacement tube assembly in the sense that has hereinbefore been described. The tube assembly 10 is designed to be easily connected to, and disconnected from, a conventional feeding formula supply tube 11 in a manner hereinafter discussed.

The inventions are illustrated here in a gastrostomy tube assembly. However, as will hereinafter be discussed, the inventions may find equally advantageous application in other tube assemblies, such as PEG and jejunostomy tubes, for example, or other corporeal access environments like suprapubic catheter assemblies.

Referring now to FIG. 2, the replacement gastrostomy tube assembly 10 is seen to comprise a short segment 15 of tube formed of silicone rubber and embodying features of the invention. The gastrostomy tube segment 15, which is constructed in a manner hereinafter discussed in detail, has a bolus 16 connected in fluid communication with the tube segment at the latter's discharge end 17, and a set connector 18 connected in fluid communication with the tube segment at the latter's inlet end 19. The bolus 16 and the set connector 18 are also formed of silicone rubber.

Adjacent the bolus tip 16, and encircling the tube segment 15 near the discharge end 17, is a tire-shaped balloon 20 which also embodies features of the invention and will hereinafter be discussed in detail. Suffice it to say at this point that the balloon 20 is filled with a fluid medium such as air or water. Air is preferred and, in the present illustration, is employed.

Approximately intermediate the ends 17 and 19 of the tube segment 15 is a right-angle bolster 21 through which the tube segment passes. The bolster 21 construction and arrangement on the tube segment 15, which comprises additional features of the invention, grips the tube segment at a selected distance from the balloon 20, and forces the segment slightly past a right angle configuration so that the set connector 18 lies immediately adjacent to the patient's abdomen when in place. The construction and operation of the bolster 21 will also hereinafter be discussed in detail.

Referring now to FIGS. 3 and 4, the bolus 16 and its connection to the discharge end 17 of the tube segment 15 is shown in substantial detail. The bolus 16 may be of the design and construction illustrated and described in the Quinn U.S. Pat. No. 5,451,216, assigned to the same assignee as the present application and invention. The bolus 16 comprises a body 30 having a tube 15 receiving section 31, a central passage section 32, and a nose section 33.

The tube segment 15, at its discharge end 17, is glued inside the receiving section 31 of the bolus 16 with a silicone based adhesive. A passage 35 extending axially through the passage section 32 of the bolus 16 is then in continuous fluid communication with the tube 15.

A radially extending discharge port 36 is formed through the bolus from the passage 35. It is through this port that enteral feeding discharge takes place.

The nose section 33 of the bolus 16 has an axial, stylet-receiving pocket 39 formed therein. In this sense the bolus 16 is different than that disclosed in the aforementioned Quinn U.S. Pat. No. 5,451,216. The pocket 39 is designed to receive the tip of a stylet (not shown in this FIGURE) in a manner hereinafter discussed in detail, both as to the way the stylet is employed and its purpose.

Referring now to FIGS. 5 and 5A, the portion of the tube segment 15 which joins the bolus 16 is shown in enlarged, longitudinal and transverse sections. The tube segment 15 comprises a silicone body 41 containing a stainless steel wire coil spring 42. The coil spring 42 extends from the receiving end (not shown) of the tube segment 15 to a point 43 immediately adjacent, but not within, the balloon 20. Accordingly, the balloon 20 surrounds a tube body portion 45 which is unsupported by the spring 42.

To form the tube segment 15, the coil spring 42 is inserted into an extruded silicone tube. Liquid silicone is introduced into the tube so that it flows the length of the tube, coating and covering the wire and adhering it to the inside of the tube. The liquid silicone sets to unitize the original tube, the coil spring 42 and the coating into a generally cylindrical wall having an inner surface 46 and an outer surface 47.

The balloon 20 is tire-shaped, as has been pointed out. It is formed of conventional silicone film which is 0.030 of an inch thick in this embodiment. Using the language of vehicle tire construction, it comprises a casing 51 having an outside diameter of 0.600 inches. The casing 51 has, at its inside diameter which corresponds to the outside diameter of the tube body 41, a pair of beads 52 and 53. The beads 52 and 53 are glued to the outer surface of the tube body 41 with a silicone adhesive in a conventional manner.

The balloon 20 is preformed in the shape illustrated. As such, air is trapped in the space 55 when assembled. The beads 52 and 53 are bonded to the tube body 41 to assemble the tube and balloon.

The side-walls 56 and 57 of the tire-shaped balloon casing 51 are preferably spaced from each other by 0.200 inches from outer surface to outer surface. The side-wall 56 extends perpendicular to the axis of the tube 15 for a distance of 0.100, i.e., it defines a substantially flat outer surface 58 extending outwardly from the bead 52 for 0.100 inches. Connecting the side walls 56 and 57 is the tread wall 59 of the casing 51. It defines a semi-circle in cross-section. The radius of the semi-circle is 0.100 inches.

The aforedescribed balloon 20 configuration provides important advantages. Its flat retention surface 58 is 50% of its diameter externally of the beads 52 and 53. In this shape it is very resistant to distortion when functioning in its tube assembly 10 retaining capacity. It also presents a wide, stable, flat retaining surface 58.

Referring now to FIGS. 6–8, the set connector 18 at the inlet end 19 of the tube 15 is shown in enlarged (FIG. 6) and then further enlarged (FIGS. 7 and 8) form. The connector 18 comprises a generally cylindrical fitting 61 also molded of silicone rubber. The fitting 61 has a unitarily formed body 62 and cap 63, with the cap flexibly attached to one end of the body by an easily bendable arm 64.

The fitting body 62 also has an axial passage 65 formed through it. Seated in the passage 65, approximately intermediate its ends, is a conventional slit valve insert 66. The valve insert 66 is also molded of silicone and includes a slit 67 which is forced open into a generally round shape by the feeding supply tube connector tip (not shown) when the tip is inserted for feeding purposes. When the tip is removed, and the valve 66 is subjected to pressure from below, the valve slit 67 closes.

The inlet end 19 of the tube 15 is seated in, and glued with a silicone adhesive to, a cylindrical end section 69 of the passage 65 in the fitting body 62. The cap 63, at the other end of the body 62, includes a plug 71 which is received in the passage 65 when it is desirable to disconnect the replacement tube assembly 10 from the feeding tube 11. An annular locking shoulder 72 is formed on the plug 71 and is adapted to snap fit into a corresponding annular locking depression encircling the passage 65.

Referring again to FIG. 2, and also to FIGS. 9–11, the construction and function of the bolster 21 will now be described. The bolster 21 comprises a molded silicone rubber body 81 and a molded silicone rubber O-ring 82. The bolster body 81 is formed in a split configuration so as to have two legs, 83 and 84, joined at corresponding one ends by a bridge 85. The legs 83 and 84 may be spread to the position shown in FIG. 9 so that the tube segment 15 is essentially straight. In this position, the O-ring 82 is positioned off the bolster, freely encircling the tube.

When the legs 83 and 84 are brought together, as seen in FIG. 2, the tube segment 15 is bent slightly past a right angle configuration, i.e., the angle is slightly less than 90° whereby the tube segment outside the bolster is actually inclined slightly toward the abdominal wall. In this position of the legs 83 and 84, the O-ring 82 is snapped into place in an annular depression 86 to maintain the bolster 21 and the tube segment 15 is this position.

FIGS. 10 and 11 show the bolster in side and end views, as taken from FIG. 9. As seen in FIGS. 9–11, the leg 83 is formed with a substantially semi-cylindrical trough 87 extending axially along one side of it. The trough 87 curves outwardly to terminate at one end at the bridge 85. At its outer end, the trough 87 becomes a cylindrical passage section 88 as it passes through an annular collar 89 which forms what amounts to a foot on the leg 83. The other leg 84 is also formed with a substantially semi-cylindrical trough 91 extending axially along one side of it. The trough 91 also curves outwardly to terminate at one end at the bridge 85. Immediately adjacent this curve, a cylindrical passage section 92 is formed through the leg 84, perpendicular to the trough 91.

The bolster 21 is fabricated by molding it in a body 81 without legs. The legs 83 and 84 are formed by cutting the body 81 on the L-shaped path best seen in FIG. 2. It will thus be seen that the normal state of the body is with the legs 83 and 84 lying flush against each other. In this relationship the two troughs 87 and 91, and the two passage sections 88 and 92, collectively form a generally L-shaped passage 95 extending entirely through the bolster, with the passage section 88 inclined slightly past a right angle. The leg 84 and, thus, the body 81 has a flat bottom or base surface 93. This bottom or base surface seats against the patient when the tube assembly 10 is in use, as seen in FIG. 1.

The tube segment 15 is threaded through the passage section 88 in the leg 83 and the passage section 92 in the leg 84 while the legs are spread into the attitude seen in FIGS. 9–11. When it is desirable to bend the tube segment 15 into slightly greater than a right-angle, in a manner hereinafter discussed, the legs 83 and 84 are simply brought together and the O-ring 82 snapped in place. Because the tube segment 15 has a coil spring 42 built into it, it does not kink and become blocked inside the bolster 21.

Figure 13:
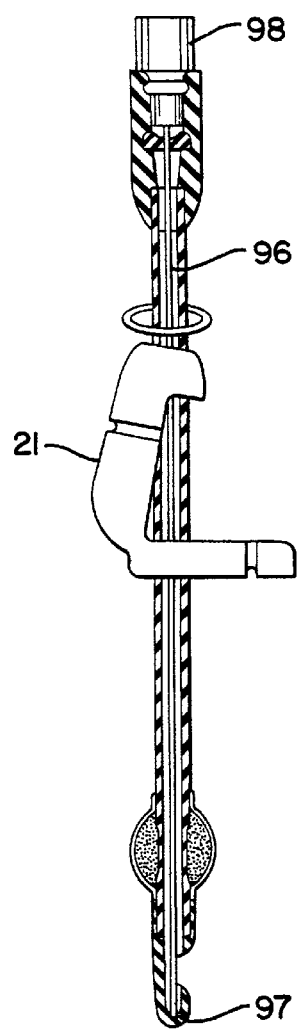
FIG. 13 is a view similar to FIG. 12, showing the stylet driven completely into the tube assembly to distend the retention balloon component immediately prior to insertion.
Figure 14:
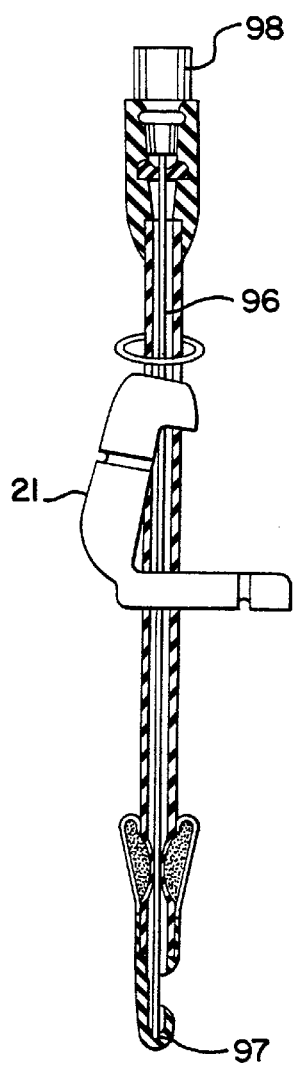
FIG. 14 is a view similar to FIG. 13, but showing the balloon component configuration as the balloon passes through the stoma.

Referring now to FIGS. 12–14 and FIG. 1, a replacement gastronomy tube assembly 10 is shown being prepared for insertion (FIGS. 12 and 13) into the patient's stomach ST through a preformed stoma S. FIG. 1 shows it inserted and secured. FIG. 14 shows it being inserted (the patient is not shown here). The stoma S has previously been formed with a PEG. When the PEG is removed, as it normally is after a short period of use, a replacement assembly is inserted.

Referring initially to FIG. 12, a rigid metal stylet 96 of known construction is inserted, tip 97 first, through the set connector 18 into the tube segment 15. The stylet 96 is inserted using its handle 98 until its tip 97 reaches and seats in the pocket 39 of the bolus 16. Further insertion of the stylet then stretches the balloon 20, as seen in FIG. 13.

According to the invention, the stylet 96 is forced into the tube segment 15 until it has stretched the balloon out into the configuration shown in FIG. 13. At this point, the volume of the balloon 20 is actually greater that it is in its relaxed form (FIG. 12) so that a partial vacuum forms within the balloon, causing it to collapse inward to some extent.

With the balloon 20 in a greatly reduced diameter form, the bolus 16 is inserted through the stoma S, followed by the balloon and the lower portion of the tube segment 15. As the balloon 20 passes through the stoma S it flattens out rearwardly into the configuration shown in FIG. 14, thus facilitating passage through the stoma. Once the balloon has clearly entered the stomach, the stylet 96 is pulled out. The balloon 20 expands to its normal size and shape as the tube segment 15 under the balloon becomes shorter and thicker again. The tube assembly 10 is then drawn outwardly until the flat surface 58 on the outer side 56 of the balloon 20 rests against the stomach wall lining. With the stylet 96 completely removed, the plug 71 is inserted into the bore 65 through the set connector for sanitary reasons.

Figure 15:
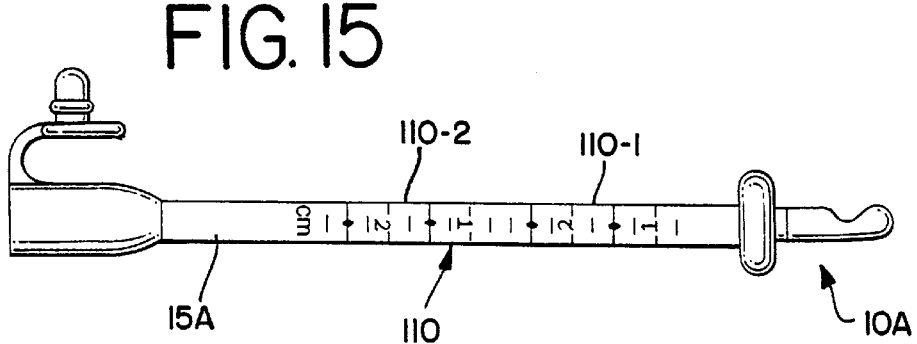
FIG. 15 is a side elevational view of a replacement tube assembly in a set of three lengths, the assembly being the shortest of the three and having a gauging system embodying features of the inventions imprinted along its length.
Figure 16:
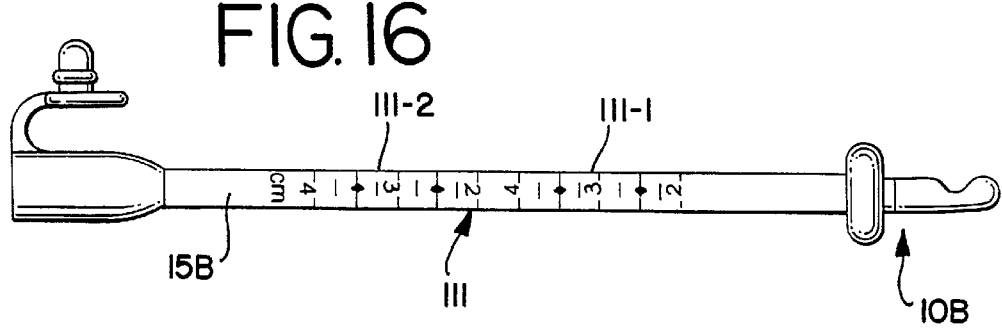
FIG. 16 is a side elevational view of the intermediate length replacement tube assembly in the set of three, also having a gauging system embodying features of the inventions imprinted along its length.
Figure 17:
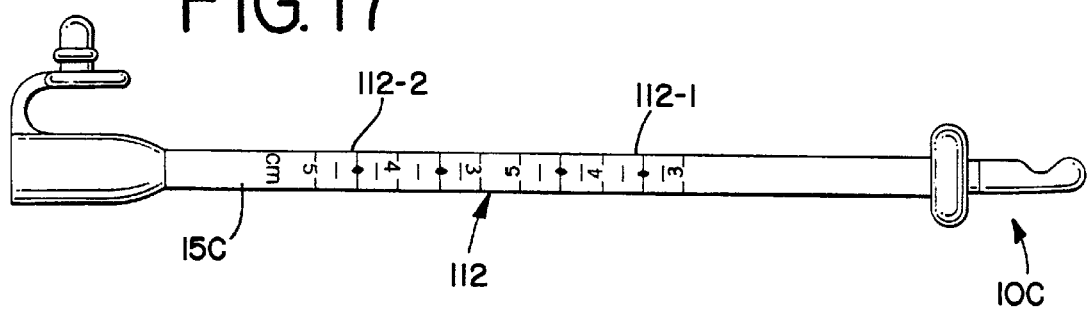
FIG. 17 is a side elevational view of the longest replacement tube assembly in the set of three, also having the gauging system imprinted along its length.

Turning now to the tube measurement system which embodies features of the inventions described and illustrated herein, attention is invited to FIGS. 15–17 which a first form of the system is shown. There, three different replacement gastronomy tube assemblies are seen at 10A, 10B and 10C. The tube assemblies 10A, 10B and 10C are identical in construction and operation to the assembly 10 hereinbefore described. As will be seen, however, the segments 15A, 15B and 15C of gastronomy tube are progressively longer (by approximately 1.25 centimeters).

In this form of the system, three different replacement assembly lengths are provided to cover the normal variations in stoma depth encountered in patients, a range of from approximately 0.75 to 5.00 centimeters. The tube 15A has a measuring gauge 110 embodying features of the invention imprinted on its side and covering the shorter-range of stoma depths of 0.75 to 2.5 centimeters. The tube 158 has a measuring gauge 111 imprinted on its side and covering the mid-range of stoma depths of 2.0 to 4.0 centimeters. The tube 15C has a measuring gauge 112 imprinted on its side and covering the upper-range of stoma depths of 3.0 to 5.0 centimeters.

As will be seen, the measuring gauge 110 comprises two identical sets of gauge markings 110-1 and 110-2 imprinted on its side. The marking set 110-2 is positioned so that corresponding centimeter gradations in the 110-1 set (1.0 centimeter, for example) are spaced precisely the length of the aforedescribed bolster passage 95 from each other, for reasons hereinafter explained. As will also be seen, the centimeter markings in the 110-1 set are read right-side-up from the bolus 16 end of the assembly while the centimeter markings in the 110-2 set are read right-side-up from the set connector 18 end, i.e., up-side-down from the bolus end.

The measuring gauges 111 and 112 each have two, identical sets of gauge markings also; markings 111-1 and 111-2 in the case of gauge 111 and 112-1 and 112-2 in the case of gauge 112. The sets in both gauges are, like the gauge 110, spaced from each other a distance corresponding to the length of the passage 95 through the bolster 21.

Figure 18:
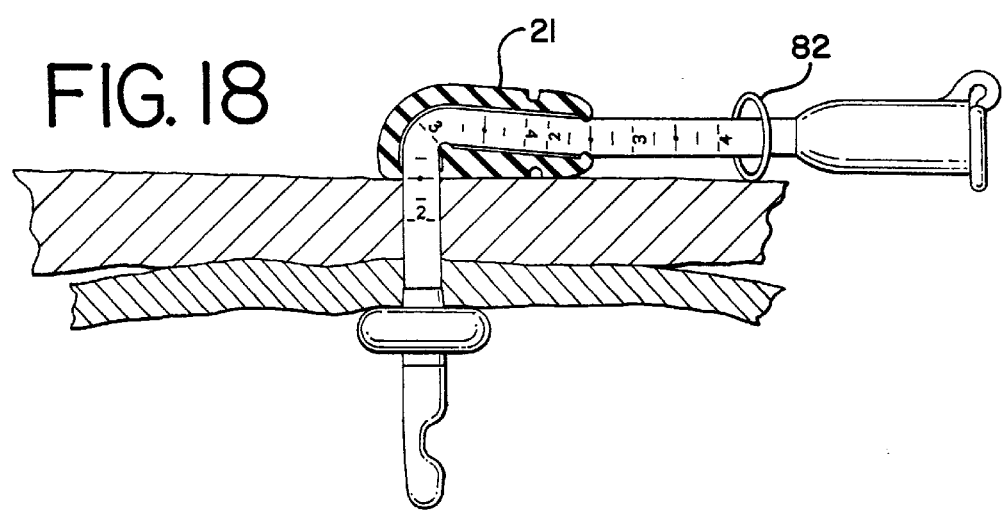
FIG. 18 is a side elevational view of a replacement tube assembly in place in a patient's stoma (in section) with the bolster positioned using the gauging system of the inventions.

Referring now to FIG. 18, with the tube assembly 111 (for example) in position so that the balloon 20 rests against the stomach lining, the physician reads the 2.5 centimeter gauge marking on the tube segment at the abdomen surface. While this is being done the bolster 21 is in its open and displaced position shown in FIGS. 12–14. Bolster legs 83 and 84 are then brought together around the silicone tube 15 and held manually. Tube segment 15 is then pulled through the bolster 21 until the paired 2.5 centimeter gauge marking is precisely aligned with the end surface of the bolster from which it has emerged. The tube segment 25 and bolster 21 position is then as seen in FIG. 18. Then the bolster legs 83 and 84 are secured by an O-ring 82. With this done, the physician knows that the flat surface 95 of the bolster 21 is resting flush against the patient's abdomen, but the balloon is not putting inordinate pressure on the stomach lining—in other words, an ideal fit has been achieved.

Figure 19:
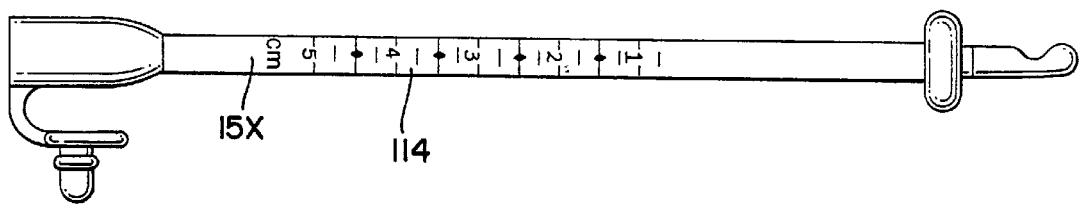
FIG. 19 is a view, similar to FIG. 17, showing a replacement tube assembly carrying a gauging system which is a variation of that shown in FIGS. 15–18.
Figure 20:
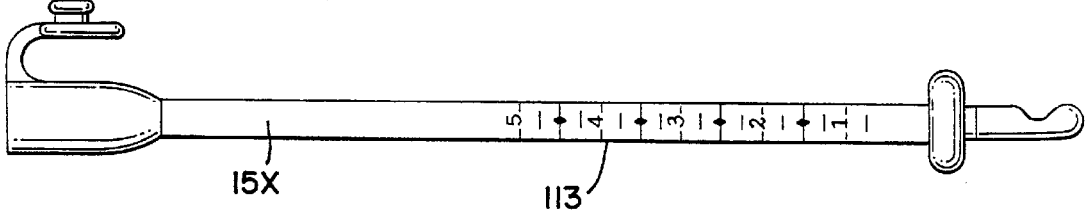
FIG. 20 is a view of the replacement tube assembly seen in FIG. 19, showing the opposite side of the tube segment and the gauging system.

Referring now to FIGS. 19 and 20, a second form of measurement system embodying features of the invention is shown. Here, one length of tube 15X is used for the full range of stoma depths. The tube 15X is the same length as the previously described tube 15C. Unlike the tube 15C, however, it has a full-range measuring gauge 113 on one side of it, with the indicia in black, and a full range measuring gauge 114 of the other side of it, with the indicia in red.

The black indicia gauge 113 measures the tube length from the balloon 20. The red indicia gauge 114, on the other side of the tube 15X, has corresponding indicia (3.0 centimeters and 3.0 centimeters, for example) spaced from each other by the length of the bolster passage 95. This second form of gauging system is used in a manner identical to that hereinbefore described in relation to the form.

Referring now to FIGS. 21–23 another embodiment of the gastronomy replacement tube assembly is illustrated generally at 210. The replacement tube assembly 210 is similar to the tube assembly 10 hereinbefore described except that it utilizes a tube segment 215 which has an inflation/deflation lumen 214 in it and a radial aperture 213 connecting that lumen with the inside of the balloon 220.

The inflation/deflation lumen 214 communicates, at its opposite end, with the set connector 218. A lumen access port 264 is formed in the body 262 of the connector 218 and a silicone rubber slit valve plug 268 seals the outer end of that port.

By inserting the round, blunt needle tip T of an inflation/ deflation needle, with a side hole, through the slit valve plug 268, the balloon 220 can either be filled with air or evacuated of air. This permits the assembly 210 to be introduced into, or removed from, a stoma even more easily.

Referring now to FIG. 24, the inventions disclosed are embodied here in a suprapubic catheter tube assembly shown generally at 310. The assembly 310 is substantially identical in construction and operation to the replacement gastrostomy tube assembly 10 hereinbefore discussed, except that it is introduced into the bladder B through the urinary urethra. It then accesses the abdominal wall through a stoma above the bladder in the pubic area. Accordingly, it is not described independently in greater detail.

Referring now to FIG. 25, a PEG tube assembly embodying features of the inventions is shown generally at 410. The PEG tube assembly 410 is, in many respects, identical to the PEG tube replacement tube assembly 10 hereinbefore discussed. To the extent that it is, the PEG tube assembly 410 features are not described in great detail. To the extent that it differs, the following discussion will be sufficient to an understanding of its construction and operation.

Turning to FIG. 26, the PEG tube assembly 410 or, more precisely, the bulk of it, begins life as a component of a PEG insertion unit 411. The PEG insertion unit 411 comprises a conventional plastic lead-in tube 412 with a solid plastic fitting 413 seated in, and glued to, one end. A placement wire 414 is anchored in the tube 412 and protrudes in a loop 416 from the other end.

The PEG tube assembly (portion) 410 seen in FIG. 26 comprises a tube segment 415 identical to that shown at 215 in FIGS. 21–23, with the exception that it has several additional features. As seen in FIG. 27, the tube segment 415 has a deflation lumen 416 extending along its length, with a radial access port 417 communicating with the retention balloon 420. The lumen 416 at the end of the tube 415 is plugged at 421 (there is no bolus attached).

The tube 415 is, in this illustration, about 25 centimeters long. At a point 10–15 centimeters from the capped end 421 a thin black marker line 425 is imprinted encircling the tube 415. Between the marker line 425 and the end 426 of the tube 415 in which the fitting 413 is glued, a wide black marker band 430 is imprinted encircling the tube.

Starting from the end 426 of the tube 415, the deflation lumen 416 is plugged at 432 with silicone rubber (after the lumen is initially formed) to a point below the band 430 but above the line 425. Below the plug 432, the lumen 416 is open to the balloon 420. It will thus be seen that the marker band 430 encircles portion of the tube 415 which does not contain an open lumen 416.

The PEG tube insertion unit 411 is pulled into the patient's stomach, in a conventional manner, by the placement wire 414. A snare wire (not shown) in a cannula (not shown) which has been inserted into the patient's stomach by piercing the abdomen and stomach walls is used to snare the placement wire loop 416 (which has been led in to the stomach through the esophagus) and pull it out through the access stoma formed by the piercing. The wire 414, lead in tube 412, and tube 415 continue to be pulled until the retention balloon 420 seats against the stomach wall.

At this point the tube 415 is severed at the marker band 430. A feeding set adaptor 435 (see FIG. 28) is then threaded into the open end of the tube 415 at the marker band 430. Before this is done, however, a bolster 441 and retention ring 482 identical to those previously discussed are placed over the tube 415, as seen in FIG. 29.

As will be seen in FIG. 28, the adaptor 435 is similar to the adaptor 18 seen in FIG. 6 except that it is threaded into the tube 415 instead of being glued onto it. This is facilitated by an externally threaded metal fitting 436 which is glued into the body 437 of the adaptor 435. The threads 438 on the fitting turn into, and are gripped by, the tube 415.

The tube 415 is now ready to be anchored to the patient's abdomen using the bolster 441 and procedure identical to that previously described. To this end the tube carries gauging indicia (not shown) which are also identical to those previously described.

After the PEG tube has been used for feeding purposes in a known manner for a period, it is removed and replaced with an aforedescribed replacement tube assembly 10. To do this the bolster 421 is opened. Then the tube 415 is cut at the black line 425. This opens the lumen 416. The retention balloon can now deflate and deform as the PEG tube assembly (or what remains of it after the feeding set adaptor end is severed) 410 is pulled out through the stoma.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

I claim:

1. A corporeal access tube assembly, comprising:
   a) a tube segment of predetermined length having a body formed of rubber-like material;
   b) said body including a wall having an inner surface and an outer surface;
   c) said inner surface defining a passage extending from one end of said tube segment to the other end of said tube segment;
   d) said body wall containing a coil spring extending along at least a portion of its length;
   e) a retention balloon fastened to and encircling said wall;
   f) a lumen in said body extending between said surfaces from a location in said tube segment where said lumen is plugged to a location adjacent said balloon where said lumen is in fluid communication with said balloon.

2. A corporeal access tube assembly, comprising:
   a) a tube segment of predetermined length having a body formed of rubber-like material;
   b) said body including a wall having an inner surface and an outer surface;
   c) said inner surface defining a passage extending from one end of said tube segment to the other end of said tube segment;
   d) said body wall containing a coil spring extending along at least a portion of its length;
   e) a retention balloon fastened to and encircling said wall;
   f) a lumen in said body extending from a location in said tube segment where said lumen is plugged to a location adjacent said balloon where said lumen is in fluid communication with said balloon; and
   g) markers on said tube segment indicating where said lumen is plugged and where said lumen is open.

3. A corporeal access tube assembly, comprising:
   a) a tube segment of predetermined length having a body formed of rubber-like material;
   b) said body including a wall having an inner surface and an outer surface;
   c) said inner surface defining a passage extending from one end of said tube segment to the other end of said tube segment;
   d) said body wall containing a coil spring extending along at least a portion of its length;
   e) a retention balloon fastened to and encircling said wall;
   f) a lumen in said body extending from a location in said tube segment where said lumen is plugged to a location adjacent said balloon where said lumen is in fluid communication with said balloon; and
   g) a set connector including a fitting for attaching said connector to said tube segment;
   h) said fitting extending into said tube segment at said one end of said tube segment;
   i) said fitting having external threads formed on it and being threaded into said portion of said body containing said coil spring.

4. The corporeal access tube assembly of claim 3 further characterized in that:
   g) said rubber-like material is silicone rubber.

5. A corporeal access tube assembly, comprising:
   a) a tube segment of predetermined length having a body formed of rubber-like material;
   b) said body including a wall having an inner surface and an outer surface;
   c) said inner surface defining a passage extending from one end of said tube segment to the other end of said tube segment;
   d) said body wall containing a coil spring extending along at least a portion of its length;
   e) a retention balloon fastened to and encircling said wall;
   f) a lumen in said body extending from a location in said tube segment where said lumen is plugged to a location adjacent said balloon where said lumen is in fluid communication with said balloon; and
   g) markers on said tube segment indicating where said lumen is plugged and where said lumen is open;
   h) said markers including indicia which marks that portion of the tube segment which contains an open lumen and indicia which marks that portion of the tube segment in which the lumen is plugged.

6. A corporeal access tube assembly, comprising:
   a) a tube segment having a body formed of rubber-like material;
   b) said body including a wall having an inner surface and an outer surface;
   c) said inner surface defining a passage extending from one end of said tube segment to the other end of said tube segment;
   d) said body wall containing a coil spring extending along at least a portion of its length; and
   e) a set connector including a fitting for attaching said connector to said tube segment;
   f) said fitting extending into said tube segment at said one end of said tube segment and having external threads formed on it;
   g) said fitting being threaded into said portion of said body containing said coil spring.

7. The corporeal access tube assembly of claim 6 further characterized in that:
   i) said rubber-like material is silicone rubber.

8. A percutaneous, endoscopic gastrostomy tube assembly, comprising:
   a) a tube segment of predetermined length having a body formed of silicone rubber;
   b) said body including a wall having an inner surface and an outer surface;
   c) said inner surface defining a passage extending from one end of said tube segment to the other end of said tube segment;
   d) said body wall containing a coil spring extending along at least a portion of its length;
   e) a retention balloon fastened to and encircling said wall at a position displaced from said one end of said tube segment;
   f) an open lumen in said body extending through at least a portion of said body wall to a location adjacent said balloon where said open lumen is in fluid communication with said balloon;
   g) said open lumen extending through said body wall only to a point displaced from said one end of said tube segment;
   h) said outer surface of said wall adjacent said one end of said tube segment having markings thereon which indicate where said open lumen is located and where said open lumen is absent from said body wall; and i) a lead-in tube connected to said one end of said tube segment.

9. The percutaneous endoscopic gastrostomy tube assembly of claim 8 further characterized in that:

j) said markings include an annular band encircling said outer surface of said wall where said open lumen is absent; and k) another annular band encircling said outer surface of said wall where said open lumen is present.

10. A corporeal access tube assembly, comprising:

a) a segment of tube having a first end and a second end;

b) said tube segment including a body wall formed of rubber-like material and having an outer surface and an inner surface;

c) said inner surface defining a generally cylindrical passage through said tube segment;

d) a wall support structure in said body wall along only a portion of said tube segment;

e) a balloon encircling another portion of said tube segment and fastened to said tube segment;

f) a bolus fastened to one end of said tube segment;

g) said bolus having a receptacle formed therein for receiving the tip of a stylet;

h) said other portion of said tube segment being stretchable by the action of a stylet seated in said receptacle so as to stretch the balloon axially and reduce its dimensions radially.

11. The corporeal access tube assembly of claim 10 further characterized in that:

i) said rubber-like material is a silicone rubber.

* * * * *